(12) United States Patent
Slattum et al.

(10) Patent No.: US 8,129,509 B2
(45) Date of Patent: Mar. 6, 2012

(54) METHOD FOR SINGLE-STEP ATTACHMENT OF A LABEL TO TARGET MOLECULES

(75) Inventors: Paul M. Slattum, Madison, WI (US); Jon A. Wolff, Madison, WI (US); James E. Hagstrom, Middleton, WI (US); Vladimir G. Budker, Middleton, WI (US)

(73) Assignee: Mirus Bio LLC, Madison, WI (US)

( * ) Notice: Subject to any disclaimer, the term of this patent is extended or adjusted under 35 U.S.C. 154(b) by 0 days.

(21) Appl. No.: 10/413,942

(22) Filed: Apr. 15, 2003

(65) Prior Publication Data

US 2004/0210044 A1 Oct. 21, 2004

Related U.S. Application Data

(62) Division of application No. 09/767,794, filed on Jan. 23, 2001, now Pat. No. 6,593,465, which is a division of application No. 08/982,485, filed on Dec. 2, 1997, now Pat. No. 6,262,252.

(51) Int. Cl.
*C07H 21/00* (2006.01)
*C07H 21/04* (2006.01)
*C07H 21/02* (2006.01)

(52) U.S. Cl. ............ 536/23.1; 536/18.7; 536/26.6; 536/25.32; 536/22.1; 530/403

(58) Field of Classification Search .......... 536/23.1, 536/18.7, 26.6, 25.32, 22.1; 530/403
See application file for complete search history.

(56) References Cited

FOREIGN PATENT DOCUMENTS

GB 769440 * 3/1957
WO WO 01/08710 A1 * 2/2001

OTHER PUBLICATIONS

Hautala et al. (Journal of the American Chemical Society, 1973, vol. 95, No. 17, pp. 5508-5514).*
Mattes et al. (Nucleic Acids Research (1986), 14 (7), 2971-87) (Abstract Sent).*
Rang et al. (Molecular Pharmacology (1970), 6(4), 357-64) (Abstract Sent).*
STN Abstract:Jacob et al. GB 769440 (Mar. 6, 1957).*
Creese et al. (Journal of Pharmacology and Experimental Therapeutics (1963), 139, 8-17) (Abstract Sent).*
Gornyak et al. (Voprosy Meditsinskoi Khimii (1986), 32 (5), 48-52) (Abstract Sent).*
Boritzki et al. (Chemical Research in Toxicology (1994), 7 (1), 41-6) (Abstract Sent).*
Elderfield et al. (Journal of Medicinal Chemistry (1967), vol. 10, No. 5, pp. 921-923).*

* cited by examiner

*Primary Examiner* — Shaojia Anna Jiang
*Assistant Examiner* — Michael C Henry
(74) *Attorney, Agent, or Firm* — Mark K Johnson

(57) ABSTRACT

Compounds and methods are provided for a single-step covalent attachment of a label to a molecule comprising forming a covalently attachable labeling reagent for alkylating the molecule. Then, combining the covalently attachable labeling reagent with a mixture containing the molecule, under conditions wherein the labeling reagent has reactivity with the molecule thereby forming a covalent bond.

3 Claims, 5 Drawing Sheets ized by a sequence of steps comprising the non-covalent
METHOD FOR SINGLE-STEP ATTACHMENT OF A LABEL TO TARGET MOLECULES This patent application is a Divisional of U.S. patent application Ser. No. 09/767,794 filed on Jan. 23, 2001, now U.S. Pat. No. 6,593,465; which is a Divisional of U.S. patent application Ser. No. 08/982,485 filed on Dec. 2, 1997, now U.S. Pat. No. 6,262,252.

The described invention relates to compounds and methods for covalently attaching a label to a target molecule. More specifically, the compounds arc alkylating compounds having a reporter molecule and the covalent attachment is performed by a one-step alkylation reaction.

BACKGROUND

The analysis and detection of minute quantities of substances in biological and non-biological samples has become a routine practice in clinical and analytical laboratories. These detection techniques can be divided into two major classes: (1) those based on ligand-receptor interactions (e.g., immunoassay-based techniques) and (2) those based on nucleic acid hybridization (polynucleotide sequence-based techniques).

Immunoassay-based techniques are characterized by a sequence of steps comprising the non-covalent binding of an antibody and an antigen complementary to it. Polynucleotide sequence-based detection techniques have been characterized by a sequence of steps comprising the non-covalent binding of a labeled polynucleotide sequence or probe to a complementary sequence of the analyte under conditions which permit hybridization of the bases through Watson-Crick pairing, and the detection of that hybridization.

The non-covalent binding of a labeled sequence or probe to a complcinenutry sequence of a nucleic acid is the primary recognition event of polynucleotide sequence-based detection techniques. This binding event is brought about by a precise molecular alignment and interaction of complementary nucleotides of the probe and target. It is energetically favored by the release of non-covalent bonding free energy, e.g., hydrogen bonding, stacking free energy and the like.

In order to employ the non-covalent binding of a probe for the determination of a nucleic acid containing a target sequence, it is necessary to be able to detect binding of the probe to the target. This detection is effected through a signaling step or event. A signaling step or event allows detection in some quantitative or qualitative manner of the occurrence of the primary recognition event.

A wide variety of signaling events may be employed to detect the occurrence of the primary recognition event. The signaling event chosen depends on the particular signal that characterizes the reporter molecule employed. Although the labeling reagent itself, without further treatment, may be detectable, more often, either the reporter molecule is attached covalently, or bound non-covalently to a labeling reagent.

There are a wide variety of reporter molecules that may be employed for covalent attachment to the labeling reagent of polynucleotide sequences useful as probes in nucleic acid detection systems. All that is required is that the reporter molecule provide a signal that may be detected by appropriate means and that has the ability to attach covalently to the labeling reagent.

Reporter molecules may be radioactive or non-radioactive. Radioactive signaling moieties are characterized by one or more radioisotopes of phosphorous, iodine, hydrogen, carbon, cobalt, nickel, and the like. Preferably the radioisotope emits .beta. or gamma. radiation, and has a long half-life. Detection of radioactive reporter molecules is typically accomplished by the stimulation of photon emission from crystalline detectors caused by the radiation, or by the fogging of a photographic emulsion.

Non-radioactive reporter molecules have the advantage that their use does not pose the hazards associated with exposure to radiation, and that special disposal techniques after use are not required. In addition, they are generally more stable, and as a consequence, cheaper to use. Detection sensitivities of non-radioactive reporter molecules may be as high or higher than those of radioactive reporter molecules.

The ability to label DNA with a non-radioactive detectable marker simply and reliably makes it attractive for use in a wide variety of molecular and cellular biology applications. Some specific applications in which a non-radioactively labeled DNA or RNA probe can be used include hybridization reaction procedures (southern, northern, slot, or dot blots, in situ hybridization), nucleic acid localization studies, DNA or RNA quantitation and DNase or RNase quantitation.

Both enzyme mediated and direct labeling protocols have been developed to attach non-radioactive detectable tags such as the fluorescent compounds fluorescein and rhodamine (and others) to DNA. While these labeling methods have allowed non-radioactive detection systems to approach or even surpass the radioactive methods in terms of sensitivity there remains significant disadvantages with each of the non-radioactive labeling systems developed to date. 1) Enzymatic DNA labeling systems require a number of reagents including both unlabeled and labeled nucleotide precursors, primers, and/or enzymes to facilitate DNA synthesis. Labeling efficiency is not easily controlled and for the two most common labeling reactions (nick translation and random priming) it is not possible to create a labeled probe that is the same size as the starting DNA. 2) Direct labeling methods also have significant limitations which include a lower efficiency of labeling resulting in reduced sensitivity, laborious multi-step labeling protocols, harsh reaction conditions, variability from reaction to reaction, and unstable reactants.

Direct labeling methods have been developed for chemically modifying nucleic acids for use as detectable probes in hybridization experiments.

Sodium bisulfite may be used in the presence of a diamine to introduce primary amines on cytosine residues which could then be subsequently modifed with a reporter group. Adarichev et al (Adarichev, V. A.; Vorobeva, N. V.; Grafodatskii, A. S.; Dymshits, G. M.; and Sablina, O. V. (1995) Molecular Biology 29(3): 538-545) used 4-aminohydroxybutylamine to transaminate cytosine residues in a similar fashion. DNA has been modified at the C-8 position of adenine or guanine using a diazonium salt attached to biotin. The diazonium salt is generated in-situ with sodium nitrite then directly reacted with DNA. In another labeling procedure, the carcinogen 2-acetylaminofluorene was modified to the reactive compound N-acetoxy-2-acetylaminofluorene by Landegent et al and attached to the C-8 position of guanine. DNA modified by this reagent was subsequently detected using antibodies directed against the modified guanosine. The reactive aldehyde at the C8 position ($N^7$-formyl group) of a ring-opened guanine has also been used as a target for direct labeling using an aldehyde reactive nucleophile such as hydrazine attached to a detectable label.

These reagents have different limitations, some of these limitations are multi-step synthesis, the ability to derivatize only single stranded DNA, the need to use large amounts of reagent or other harsh conditions to get adequate amounts of DNA modification, and the modification of amines involved in double-stranded DNA base pairing.

The techniques of Northern and Southern blotting are two of the most powerful and frequently used procedures in molecular biology. Yet the necessary manipulations are time consuming and are not likely to be automated under current technology. Often the polynucleotide (RNA, DNA) under analysis must first be fractionated by size, transferred onto a solid support and then treated through a series of steps to ensure only specific binding of a probe. Detection of the hybridized products usually depends on radiolabeling, heavy metal derivatization or antibody complexation. The methods of blotting have been a staple of basic research, and now also serve in an ever increasing number of commercial kits used to diagnose genetic, malignant, and infectious diseases.

In 1967 Belikova et al. (Belikova, A. M., Zarytova, V. F. and Grineva, N. I. (1967) Tetrahedron Letters, 37:3557-62) first described monoadduct alkylation of ribonucleosides and diribonucleoside phosphates using 2-chloroethylamine residues. While this work provided evidence that ribonucleosides could be covalently modified with the alkylating mustard derivative, the efficiency of the process was very low. Utilizing a multi-step process Frumgarts et al. (Frumgarts, L. A.; Kipriyanov, S. M.; Kalachikov, S. M.; Dudareva, N. A.; Dymshits, G. M.; Karpova, G. G.; and Salganik, R. I. (1986) Bioorg. Khim. 12(11): 1508-1513) alkylated DNA using the nitrogen mustard 4-(N-methylamino-N-2-chloroethyl) benzylamine, and subsequently attached fluorescent labels to the amine that had been covalently attached to the DNA. This multi-step process required that the mustard and fluorescent label be used in a large molar excess to the DNA being labeled.

Quinicrine (acridine) is a DNA intercalating molecule which is also fluorescent. Caspersson et al. used this molecule both with and without the attachment of a nitrogen mustard to obtain chemical and physicochemical information about metaphase chromosomal structure. In this study, the fluorescent pattern obtained using quinicrine, which contains no alkylating group, produced a band pattern of the same type as the quinicrine mustard. (Caspersson, T.; Zech, L.; Modest, E. J.; Foley, G. E.; Wagh, U.; and Simonsson, (1969) E. Experimental Cell Research 58 128-140).

SUMMARY

Utilizing the nucleic acid alkylating ability of the nitrogen mustards we have developed a series of labeling reagents consisting of 1) a nitrogen mustard moiety, 2) a cationic linker and 3) a detectable marker. A nucleic acid reactive nitrogen mustard derivative used in the synthesis of these labeling agents can be the aromatic nitrogen mustard 4-[(2-chloroethyl)-methylamino]-benzaldehyde. This nitrogen mustard derivative was described in U.S. Pat. No. 2,141,090.

The ideal labeling method would combine one step simplicity with high efficiency labeling that results in a labeled product that remains intact, stable and the same size as the starting DNA. To develop a labeling reagent with these characteristics we used nitrogen mustards having the ability to alkylate DNA in a one step reaction resulting in DNA containing a covalently attached adduct.

The procedure for labeling results in the formation of a chemical bond between the compound and the polynucleic acid and/or protein. The labeling procedure consists of incubating the polynucleic acid with the said compounds in aqueous or non-aqueous solutions, followed by separation of the labeled polynucleic acid from the unreacted labeling reagent. The extent of labeling can be controlled by regulating the relative amounts of labeling reagent and polynucleic acid, by adjusting the length of the incubation, by controlling the temperature of the incubation, by controlling the absolute concentrations of polynucleic acid and labeling reagent, and by controlling the composition of the aqueous or organic solution using solvent, pH, ionic strength, and buffers.

The labeled polynucleic acid can be used for several purposes:

1) techniques to detect specific sequences of polynucleic acids that rely upon hybridization or binding affinity of the labeled polynucleic acid to target nucleic acid or protein; including dot blots, slot blots, Southern blots, Northern blots, Southwestern blot, FISH (fluorescent in situ hybridization), in situ hybridization of RNA and DNA sequences, and newly developing combinatorial techniques in which the polynucleic acid is on a "chip" or multiwell or multislot device.
2) labeling polynucleic acids that are delivered to cells in vitro or in vivo so as to determine their sub-cellular and tissue location
3) labeling oligonucleotides that are used as primer in amplification techniques such as PCR (polymerase chain reaction)
4) quantitating polynucleic acids
5) quantitating nucleases (including RNases and DNases) by fluorescence polarization or fluorescence dequenching.
6) sequencing polynucleic acids
7) directly detecting mutations
8) covalently attaching reactive groups for use in anti-sense applications Also described is a method of functionalizing digoxin. Digoxin is functionalized by first oxidizing the diol functionality on the terminal sugar residue forming digoxin di-aldehyde, and subsequent reductive alkylation using sodium cyanoborohydride and a linking compound. The linker consists of an organic molecule with a primary amine and a protected primary amine, which after removal of the protecting group results in a digoxin derivative with a primary amino group. The primary amine can be transformed into a thiol reactive group such as a haloacetamide, a maleimide, a disulfide, or a pyridyldithio; an aldehyde or ketone reactive group such as a thiosemicarbazide or a hydrazide; an amine reactive group such as a succinimidyl ester, isothiocyanate, or sulfonyl chloride; or a carboxylic acid reactive group such as a diazomethane or a haloacetyl. This methodology results in a digoxin molecule that can be used to label proteins, peptides, polysaccharides, lipids, and other molecules of interest. The straight-forward synthesis from inexpensive precursors also lends utility to this unique method of supplying a digoxin label.

A method is provided for a single-step covalent attachment of a label to a nucleic acid comprising forming a covalently attachable labeling reagent for alkylating the nucleic acid. Then, combining the covalently attachable labeling reagent with a mixture containing the nucleic acid, under conditions wherein the labeling reagent has reactivity with the nucleic acid thereby forming a covalent bond.

A compound is provided that is a labeling molecule comprising a covalently attachable labeling reagent for alkylating a chemical in a single-step reaction, thereby providing the chemical with a detectable reporter molecule.

In a preferred embodiment, a compound is provided having the structure comprising

D-B-A wherein, D is selected from the group consisting of fluorescence-emitting compounds, radioactive compounds, haptens, immunogenic molecules, chemiluminescence-emitting compounds, and proteins; B is selected from the group of molecules having an affinity for nucleic acids by interactions consisting of electrostatic, minor groove binding, major groove binding, and intercalation; and, A is selected from the group of alkylating agents consisting of mustards and three-membered ring derivatives.

In a preferred embodiment, a compound having the general structure comprising

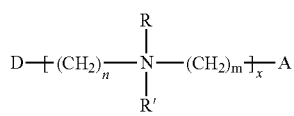

wherein, D is selected from the group consisting of fluorescence-emitting compounds, radioactive compounds, haptens, immunogenic molecules, chemiluminescence-emitting compounds, and proteins; R is selected from the group of alkyls and hydrogen; R' is selected from the group of alkyls and hydrogen; n is an integer from 1 to 20; m is an integer from 1 to 20; x is an integer from 1 to 5; and, A is selected from the group of alkylating agents consisting of mustards and three-membered ring derivatives.

Also provided is a kit comprising a receptacle containing a covalently attachable labeling reagent for alkylating a chemical in a single-step reaction. Instructions for use are also provided with the kit. By the term instructions for use, it is meant a tangible expression describing the reagent concentration for at least one assay method, parameters such as the relative amount of reagent and sample to be admixed, maintenance time periods for reagent/sample admixtures, temperature, buffer conditions and the like.

Reference is now made in detail to the preferred embodiments of the invention, examples of which are illustrated in the accompanying drawings.

DETAILED DESCRIPTION

Figure 1A:
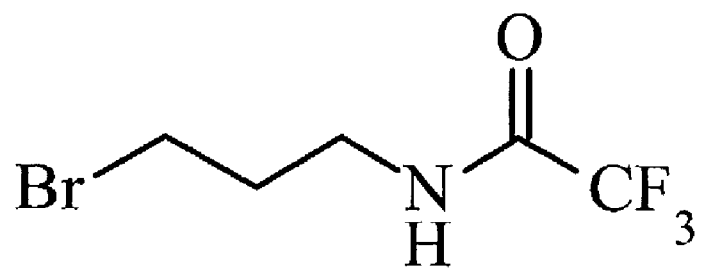
FIG. 1(a) is an illustration of the chemical structure for 3-bromo-1-(trifluoroacetamidyl)propane.

Definitions:

alkylating—a chemical reaction that results in the attachment of an alkyl group to the substance of interest, a nucleic acid in a preferred embodiment.

alkyl group—an alkyl group possesses an $sp^3$ hybridized carbon atom at the point of attachment to a molecule of interest.

anti-sense—oligonucleotide that has sequence complementary to specific sequence of mRNA.

aziridine—A three-membered ring containing one nitrogen atom.

enzyme—enzymes are proteins evolved by the cells of living organisms for the specific function of catalyzing chemical reactions.

aqueous or non-aqueous solutions—Aqueous solutions contain water. Non-aqueous solutions are made up of organic solvents bifunctional—A molecule with two reactive ends. The reactive ends can be identical as in a homobifunctional molecule, or different as in a heterobifucnctional molecule.

buffers—Buffers are made from a weak acid or weak base and their salts. Buffer solutions resist changes in pH when additional acid or base is added to the solution.

combinatorial techniques—Techniques used to prepare and to screen extremely large pools of polynucleic acid sequences in which the sequences are immobilized in known positions on "chips", multiwell devices, multislot devices, beads, or other devices capable of segregating the polynucleic acid sequences.

CPI moiety—Family of which alkylate double stranded DNA without cross-reactions with single stranded DNA, RNA, proteins or other nucleophile containing groups. The drug is a derivative of a naturally occurring antibiotic which binds double stranded DNA in the minor groove. All compounds in the CPI family include the functionality: 1,2,8,8a-tetrahydro-7-methylcyclopropa-[c]pyrrolo-[3,2-e]indol-4 (5H)-one

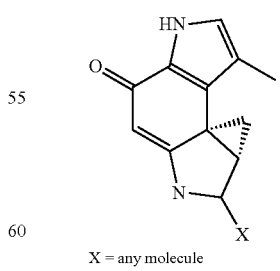

X = any molecule crosslinking—The chemical attachment of two or more molecules with a bifunctional reagent.

cyclopropane—A three-membered ring made up of all carbon atoms.

electrostatic interactions—The non-covalent association of two or more substances due to attractive forces between positive and negative charges.

episulfide—A three-membered ring containing one sulfur atom.

FISH—in situ hybridization technique in which the probe is labeled with a fluorescent marker.

fluorescence dequenching—technique monitoring the reappearence of fluorescent intensity when said fluorescence that had been previously quenched from having been in close proximity to another fluorescent molecule is released from close proximity to the other fluorescent molecule.

hapten—A small molecule that cannot alone elicit the production of antibodies to it. However, when covalently attached to a larger molecule it can act as an antigenic determinant, and elicit antibody synthesis.

hybridization—Highly specific hydrogen bonding system in which guanine and cytosine form a base pair, and adenine and thymine (or uracil) form a base pair.

In Situ Hybridization—hybridization using the labeled polynucleic acid probe taking place at the site of the immobilized polynucleic acid target within the context of the cell.

intercalating group—A chemical group characterized by planar aromatic ring structures of appropriate size and geometry capable of inserting themselves between base pairs in double-stranded DNA.

labeling—attachment of a reporter molecule via a chemical bond to a compound of interest such as a polynucleic acid or protein.

labeling reagent—a compound containing a reporting molecule that can be covalently attached to a polynucleic acid or a protein minor groove binding group—A chemical group with an affinity for the minor groove of double stranded DNA through non-covalent interactions.

major groove binding group—A chemical group with an affinity for the major groove of double stranded DNA through non-covalent interactions.

mustards—include nitrogen mustards and sulfur mustards. Mustards are molecules consisting of a nucleophile and a leaving group separated by an ethylene bridge. After internal attack of the nucleophile on the carbon bearing the leaving group a strained three membered group is formed. This strained ring (in the case of nitrogen mustards an aziridine ring is formed) is very susceptible to nucleophilic attack. Thus allowing mustards to alkylate weak nucleophiles such as polynucleic acids. Mustards can have one of the ethylene bridged leaving groups attached to the nucleophile, these molecules are sometimes referred to as half-mustards; or they can have two of the ethylene bridged leaving groups attached to the nucleophile, these molecules can be referred to as bis-mustards. Examples:

nitrogen mustard—A molecule that contains a nitrogen atom and a leaving group separated by an ethylene bridge, i.e. $R_2NCH_2CH_2X$ where R=any chemical group, and X–a leaving group typically a halogen. In general:

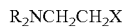
$R_2NCH_2CH_2X$

R=any chemical group
N=nitrogen
X=a leaving group, typically a halogen
aromatic nitrogen mustard

$RR'NCH_2CH_2X$

R=any chemical group
N=nitrogen
X=a leaving group, typically a halogen
R'=an aromatic ring
R=any chemical group
bis nitrogen mustard

$RN(CH_2CH_2X)_2$

R=any chemical group
N=nitrogen
X=a leaving group, typically a halogen
sulfur mustard

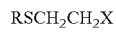
$RSCH_2CH_2X$

R=any chemical group
S=sulfur
X=a leaving group, typically a halogen
aromatic sulfur mustard

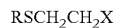
$RSCH_2CH_2X$

R=an aromatic ring
S=sulfur
X=a leaving group, typically a halogen
bis sulfur mustard

$S(CH_2CH_2X)_2$

S=sulfur
X=a leaving group, typically a halogen oligonucleotide—a polynucleic acid with 30 or less base-sugar-phosphate groups.

oxirane—A three-membered ring containing one oxygen atom, also called an epoxide.

protein—a molecule made up of 2 or more amino acids. The amino acids may be naturally occuring or synthetic.

polynucleic acids—refers to a string of at least two base-sugar-phosphate combinations. Natural nucleic acids have a phophate backbone, artificial nucleic acids may contain other types of backbones, but contain the same bases. Nucleotides are the monomeric units of nucleic acid polymers. The term includes deoxyribonucleic acid (DNA) and ribonucleic acid (RNA). RNA may be in the form of an tRNA (transfer RNA), snRNA (small nuclear RNA), rRNA (ribosomal RNA), mRNA (messenger RNA), anti-sense RNA, and ribosymes. DNA may be in form plasmid DNA, viral DNA, linear DNA, or chromosomal DNA or derivatives of these groups. In addition these forms of DNA and RNA may be single, double, triple, or quadruple stranded. The term also includes PNAs (peptide nucleic acids), phosphothionates, and other variants of the phosphate backbone of native polynucleic acids.

polynucleotide—a polynucleic acid with more than 30 base-sugar-phosphate groups.

photochemical—Refers to a reaction that requires a light source for initiation of reaction.

reporter or marker molecules—Chemical (organic or inorganic) molecules or groups capable of being detected, and in some cases, quantitated in the laboratory. Reporter molecules include, but are not limited to fluorescence-emitting molecules (which include fluoresceins, rhodamines, pyrenes, lucifer yellow, BODIPY® (4,4-difuoro-4-bora-3a,-4a-diaza-s-indacene derivatives), malachite green, coumarins, dansyl derivatives, mansyl derivatives, dabsyl drivatives, NBD flouride, stillbenes, anthrocenes, acridines, rosamines, TNS chloride, ATTO-TAG™, Lissamine™ derivatives, eosins, naphthalene derivatives, ethidium bromide derivatives, thiazole orange derivatives, ethenoadenosines, CyDyes$^{fu}$ (cvanine derivatives), aconitine, Oregon Green, Cascade Blue, and other fluorescent molecules), radioactive molecules, immunogenic molecules, haptens, such as digoxin, affinity molecules such as biotin which binds to avidin and streptavidin, chemiluminescence-emitting molecules, phosphorescent molecules, oligosaccharides which bind to lectins, or a protein or an enzyme such as alkaline phosphatase. The reporter molecule may also contain radioactive atoms such as $H^3$, $C^{14}$, $P^{32}$, $P^{33}$, $S^{35}$, $I^{125}$, $I^{131}$, $Tc^{99}$, and other radioactive elements.

salts—Salts are ionic compounds that dissociate into cations and anions when dissolved in solution. Salts increase the ionic strength of a solution, and consequently decrease interactions between polynucleic acids with other cations.

single-step covalent attachment—a reaction set up to take place after all of the reagents necessary to perform covalent attachment are placed in contact with each other in a receptacle, without further steps.

target—The specific sequence of bases in a nucleic acid present in an analyte whose presence is to be detected.

Dot Blots—Technique in which the polynucleic acid is immobilized on a nylon membrane or nitrocellulose filter before being probed with labeled polynucleic acid.

Slot Blots—Technique in which the polynucleic acid is immobilized on a nylon membrane or nitrocellulose filter using a slot blot apparatus before being probed with labeled polynucleic acid.

Southern Blot—Technique in which the polynucleic acid (DNA) is transferred from an agarose gel to a nylon membrane or a nitrocellulose filter before being probed with labeled polynucleic acid.

Northern Blot—Technique in which the polynucleic acid (RNA) is transferred from an agarose gel to a nylon membrane or a nitrocellulose filter before being probed with labeled polynucleic acid.

Southwestern Blot—Technique in which protein is transferred from an acrylamide gel to a nylon membrane or a nitrocellulose filter before being probed with labeled polynucleic acid.

R-chloride—Is the aromatic nitrogen mustard 4-[(2-chloroethyl)-methylamino]-benzylamine R-aldehyde—Is the aromatic nitrogen mustard 4-[(2-chloroethyl)-methylamino]-benzaldehyde One can determine whether or not a particular compound is suitable for the present invention by comparing the candidate compound with successful compounds illustrated in the examples. A suitable alkylating compound will alkylate a target molecule in a one-step reaction. The examples demonstrate suitable methods and preparation of compounds for successful alkylation of target molecules. If a candidate compound performs to at least 80% of the efficiency of the compounds described in the examples, the compound is a suitable one-step alkylating compound.

According to a preferred embodiment of present invention, a nucleic acid molecule with a nucleotide sequence, which may be complementary to that of a target sequence, is converted into a labeling compound by covalently attaching a reporter molecule. Several compounds are described that are useful for attaching reporter molecules to nucleic acids and proteins. In a preferred embodiment a compound suitable for use with the present invention consists of one or more of the following three parts:

A—alkylating group—chemical functionalities that are electrophilic, allowing them to become covalently attached to compounds bearing a nucleophilic group. Alkylating reagents include mustards (nitrogen mustards and sulfur mustards ); and three-membered rings (aziridines, oxiranes, cyclopranes, activated cyclopropanes, and episulfides)

B—Spacer—a connection between the alkylating group and the reporter molecule—a spacer group that includes alkanes, alkenes, esters, ethers, glycerol, amide, saccharides, polysaccharides, heteroatoms such as oxygen, sulfur, or nitrogen, and/or a molecule that is cleavable under physiologic conditions such as a disulfide bridge or an enzyme-sensitive group. The spacer may bear a net positive charge, or be any of the following: minor groove binders, major groove binders, intercalating groups, or other DNA-binding proteins or peptides such as transcription factors thereby providing the compound with an increased affinity for polynucleic acids. The spacer is provided to alleviate possible molecular interference by separating the reporter molecule from the alkylating compound as well as nucleic acids after alkylation.

C—reporter molecule—a chemical moiety attached to the compound for purposes of detection. The reporter molecule may be fluorescent, such as a rhodamine or flourescein derivative. The reporter molecule may be a hapten, such as digoxin, or a molecule which binds to another molecule such as biotin which binds to avidin and streptavidin or oligosaccharides which bind to lectins. The reporter molecule may be a protein or an enzyme such as alkaline phosphatase. The reporter molecule may also contain radioactive atoms such as $H^3$, $C^{14}$, $P^{32}$, $P^{33}$, $S^{35}$, $I^{125}$, $I^{131}$, $Tc^{99}$, and other radioactive elements.

In another preferred embodiment are several compounds that are useful for crosslinking polynucleic acids and proteins to other compounds including reporter molecules, proteins, lipids, and polynucleic acids. In a preferred embodiment a compound suitable for use with the present invention consists of one or more of the following three parts:

A—alkylating group—chemical functionalities that are electrophilic, allowing them to become covalently attached to compounds bearing a nucleophilic group. Alkylating reagents include mustards (nitrogen mustards and sulfur mustards ); and three-membered rings (aziridines, oxiranes, cyclopranes, activated cyclopropanes, and episulfides)

B—Spacer—a connection between the alkylating group and the reporter molecule—a spacer group that includes alkanes, alkenes, esters, ethers, glycerol, amide, saccharides, polysaccharides, heteroatoms such as oxygen, sulfur, or nitrogen, and/or a molecule that is cleavable under physiologic conditions such as a disulfide bridge or an enzyme-sensitive group. The spacer may bear a net positive charge, or be any of the following: minor groove binders, major groove binders, intercalating groups, or other DNA-binding proteins or peptides such as transcription factors thereby providing the compound with an increased affinity for polynucleic acids.

C—reactive group a chemical functionality capable of undergoing further chemical reactions. Reactive groups include, but are not limited to alkylating groups, amines, alcohols, sulfhydryls, isothiocyanates, isocyanates, acyl azides, N-hydroxysuccinimides, sufonyl chlorides, aldehydes, epoxides, carbonates, imidoesters, carboxylates, alkylphosphates, arylhalides (such as difluoro-dinitrobenzene), iodoacetamides, maleimides, aziridines, acryloyl chlorides, flourobenzes, disulfides, succinamides, carboxylic acids, and activated carboxylic groups.

In another preferred embodiment is a method for labeling polynucleic acids using a compound suitable for use with the present invention consisting of one or more of the following three parts:

A—alkylating group—chemical functionalities that are electrophilic, allowing them to become covalently attached to compounds bearing a nucleophilic group. Alkylating reagents include mustards (nitrogen mustards and sulfur mustards); and three-membered rings (aziridines, oxiranes also known as epoxides, cyclopranes, activated cyclopropanes, and episulfides)

B—Spacer—a connection between the alkylating group and the reporter molecule—a spacer group that includes alkanes, alkenes, esters, ethers, glycerol, amide, saccharides, polysaccharides, heteroatoms such as oxygen, sulfur, or nitrogen, and/or a molecule that is cleavable under physiologic conditions such as a disulfide bridge or an enzyme-sensitive group. The spacer may bear a net positive charge, or be any of the following: minor groove binders, major groove binders, intercalating groups, or other DNA-binding proteins or peptides such as transcription factors thereby providing the compound with an increased affinity for polynucleic acids.

C—reporter molecule—a reporter molecule—a chemical moiety attached to the compound for purposes of detection. The reporter molecule may be fluorescent, such as a rhodamine or flourescein derivative. The reporter molecule may be a hapten, such as digoxin, or a molecule which binds to another molecule such as biotin which binds to avidin and streptavidin or oligosaccharides which bind to lectins. The reporter molecule may be a protein or an enzyme such as alkaline phosphatase. The reporter molecule may also contain radioactive atoms such as $H^3$, $C^{14}$, $P^{32}$, $P^{33}$, $S^{35}$, $I^{125}$, $I^{131}$, $Tc^{99}$, and other radioactive elements.

Any of a large number of nucleic acid sequences may be employed in accord with this invention for use as probes in the detection of target molecules. Included, for example, are target sequences in both RNA and DNA, as are the polynucleotide sequences that characterize various viral, viroid, fungal, parasitic or bacterial infections, genetic disorders or other sequences in target molecules that are desirable to detect. Probes may be of synthetic, semi-synthetic or natural origin. Probe molecules include both polyribonucleotides and polydeoxyribonucleotides.

Although the presently preferred embodiment employs nucleic acids of approximately 30 base pairs or longer, shorter nucleic acids may be used, provided they are capable of specifically and stably hybridizing to a target sequence. The nucleic acids may be designed to hybridize to either the sense or antisense strand of a DNA duplex. When the target is messenger RNA, however, the sequence of the probe should be complementary to it.

Synthesis

The synthetic methodology used to prepare the labeling reagents of the invention is described below. The structures of these compounds are included in FIG. 1.

FIG. 1(a): Preparation of
3-bromo-1-(trifluoroacetamidyl)propane

To a solution of 3-bromopropylamine (2.19 g, 10.0 mmol, Aldrich Chemical Co., Milwaukee, Wis.) and triethyl amine (1.67 mL, 12.0 mmol, Aldrich Chemical Co.) in 60 mL methylene chloride at 0° C. in a 200 mL roundbottom flask equipped with a addition funnel was added trifluoroacetic anhydride (1.69 mL, 12.0 mmol, Aldrich Chemical Co.) in 60 mL methylene chloride over a period of 20 minutes. The reaction was stirred overnight, washed 1×10 mL 2% bicarbonate, 1×10 mL water, and dried over magnesium sulfate. Removal of solvent yielded 2.07 g (88.5%) product as amorphous crystals. $H^1$-NMR ($CDCl_3$)): ? 3.55 (m, 2H), 3.45 (m, 2H), 2.17 (m, 2H).

Figure 1B:
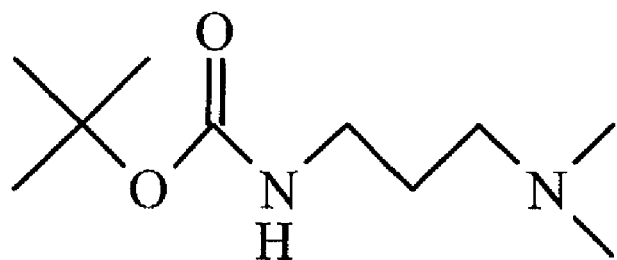
FIG. 1(b) is an illustration of the chemical structure for N,N-dimethyl-N-[N'-(tert-butoxycarbonyl)-3-aminopropylamine].

FIG. 1(b): N,N-dimethyl-N-[N'-(tert-butoxycarbonyl)-3-aminopropylamine]

3-dimethylaminopropylamine (251 µL, 204 mg, 2.00 mmol, Aldrich Chemical Co.) was combined with diisopropylamine (348 µL, 2.00 mmol, Aldrich Chemical Co.) in 2 mL tetrahydrofuran. BOC-ON (542 mg, 2.20 mmol, Aldrich Chemical Co.) was added to the stirring reaction mixture. The reaction mixture was stirred at room temperature for 12 hours. Following removal of THF on a rotary evaporator the residue was dissolved in 30 mL diethyl ether, washed 3×2 N NaOH, and dried over $MgSO_4$. Solvent removal yielded 359 mg (88.7%) product as a colorless oil. $H^{1-}$-NMR ($CDCl_3$): δ 5.16 (bs, 1H), 3.76 (m, 2H), 2.30 (m, 2H), 2.21 (s, 6H), 1.65 (m, 2H), 1.44 (s, 9H).

Figure 1C:
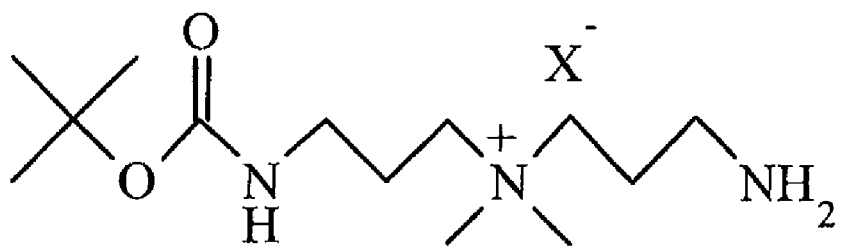
FIG. 1(c) is an illustration of the chemical structure for N-[N'-(tert-butoxycarbonyl)-3-aminopropyl]-N,N-dimethyl-3-aminopropylammonium salt

FIG. 1(c): N-[N'-(tert-butoxycarbonyl)-3-aminopropyl]-N,N-dimethyl-3-aminopropylammonium carbonate FIG. 1(b) (344 mg, 1.70 mmol) and FIG. 1(a) ( 433 mg, 1.85 mmol) were combined in 250 µL anhydrous dimethylformamide (DMF), and incubated at 55° C. for 48 hours. Product was precipitated from the reaction mixture by the addition of diethyl ether. Product was dried under vacuum yielding 686 mg (92.5%) product as a colorless oil. $H^1$-NMR ($D_2O$): δ 7.95 (s, 1H), 3.45 (m, 2H), 3.35 (m, 4H), 3.20 (m, 2H), 3.10 (s, 6H), 2.10 (m, 2H), 1.95 (m, 2H), 1.45 (s, 9H). The triflouroacetamide group was cleaved by dissolving the reaction product (179 mg, 0.409 mmol) in 1.0 mL methanol and 0.5 mL water. Sodium carbonate (173 mg, 4.09 mmol) was added and the reaction was stirred at room temperature for 12 hours. The carbonate was removed by centrifugation. Product was dissolved in methanol and precipitated by the addition of diethyl ether yielding 93.5 mg (66.5%) product as a colorless solid. TLC: silica gel; water/acetic acid/ethyl acetate; 2/2/1; Rf=0.61, developed using Dragendorff's Reagent. $H^{1-}$NMR ($CD_3OD$): δ 3.37 (m, 4H), 3.15 (m, 8H), 2.73 (m, 2H), 1.94 (m, 4H), 1.44 (s, 9H).

Figure 1D:
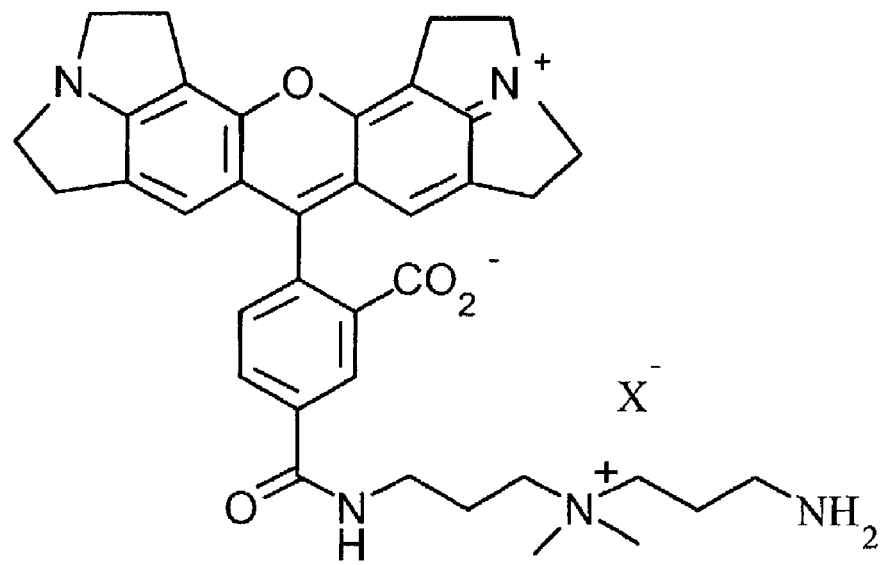
FIG. 1(d) is an illustration of the chemical structure for N-[N'-(5-(and-6)-carboxy-X-rhodaminecarbonyl)-3-aminopropyl]-N,N-dimethyl-3-aminopropylammonium salt.

FIG. 1(d): N-[N'-(5-(and-6)-carboxy-X-rhodaminecarbonyl)-3-aminopropyl]-N,N-dimethyl-3-aminopropylammonium di-trifluoroacetate salt To a solution of 5-(and-6)-carboxy-X-rhodamine, succinimidyl ester (125 mg, 198 µmol, Molecular Probes) in 0.5 mL DMF was added FIG. 1(c) (63.6 mg, 198 µmol) and diisopropylethylamine (69.2 µL, 396 µmol, Aldrich Chemical Co.) in 3.0 mL DMF. The reaction was stirred at room temperature for approximately 1 hour. The product was isolated by precipitation with diethyl ether. The tert-butoxy carbonyl (BOC) group was removed by dissolving the residue in triflouroacetic acid(TFA), and incubating at room temperature for 20 minutes. The TFA was removed under a stream of $N_2$, and the residue was purified via HPLC (C-18: acetonitrile/0.1% TFA) to yield 107 mg (63.7%) product as a red solid. TLC: silica gel; acetonitrile/10% acetic acid; 3/1; Rf=0.30. $H^1$-NMR ($CD_3OD$) ? 8.75 (m, 1H), 8.25 (m, 1H), 7.45 (m, 1H), 6.60 (s, 2H), 3.50 (m, 8H), 3.15 (s, 6H), 3.05 (m, 4H), 2.65 (m, 4H), 2.20 (m, 4H), 2.10 (m, 4H), 1.95 (m, 4H).

Figure 1E:
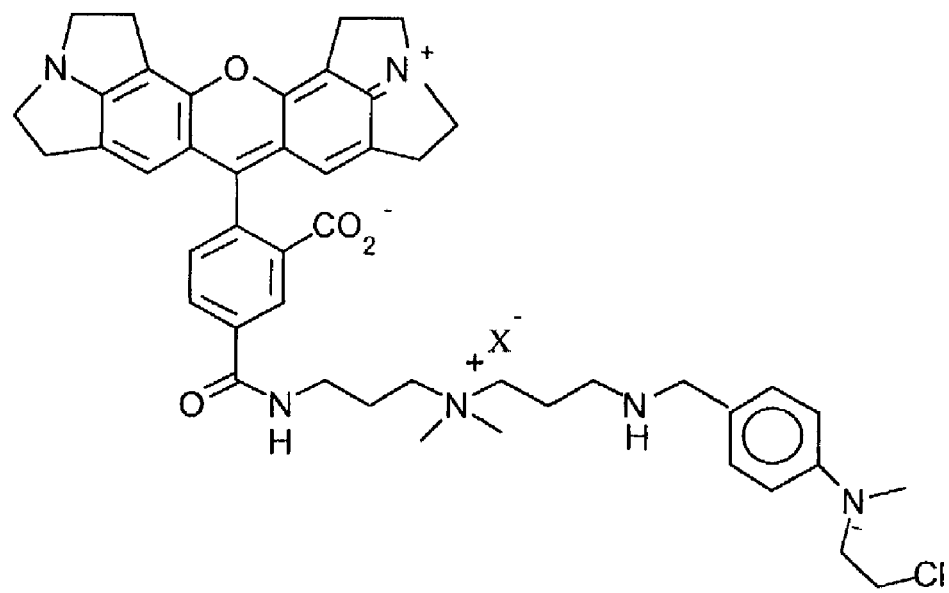
FIG. 1(e) is an illustration of the chemical structure for N-[N'-(5-(and-6)-carboxy-X-rhodaminecarbonyl)-3-aminopropyl]-N,N-dimethyl-3-N'''-{4-[(2-chloroethyl)-methylamino]-benzylamine}aminopropylammonium salt
Figure 1F:
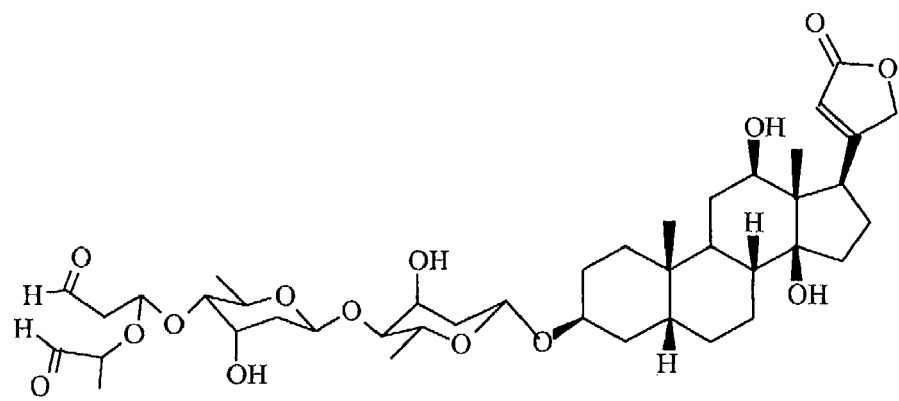
FIG. 1(f) is an illustration of the chemical structure for digoxin dialdehyde.
Figure 1G:
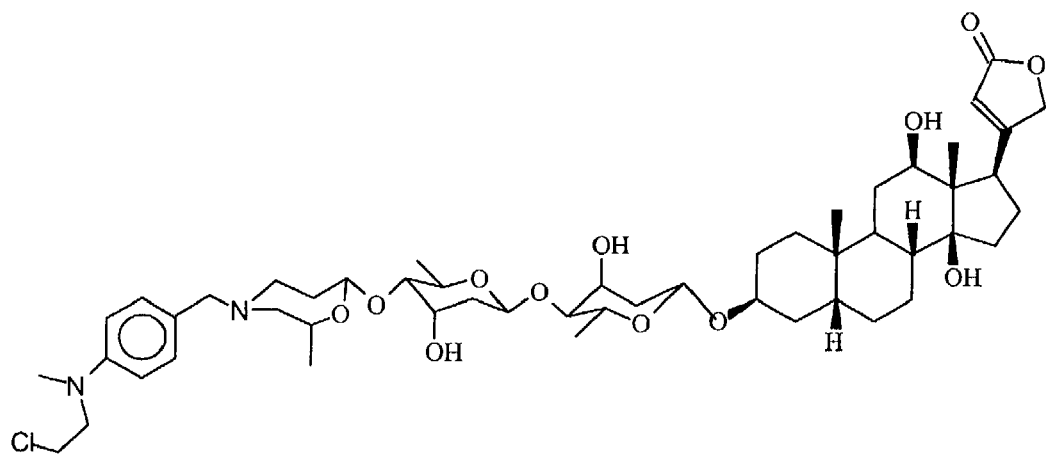
FIG. 1(g) is an illustration of the chemical structure for digoxin labeling reagent.
Figure 1H:
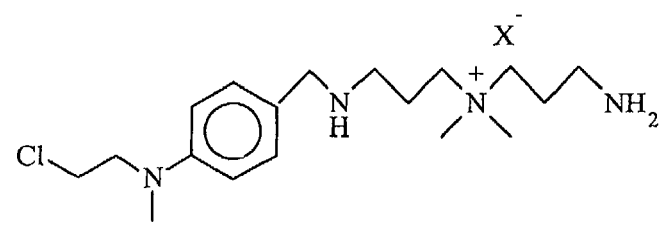
FIG. 1(h) is an illustration of the chemical structure N-[N'-{4-[(2-chloroethyl)-methylamino]-benzylamine}-3-aminopropyl]-N,N-dimethyl-3-aminopropylammonium salt.

FIG. 1(e): N-[N'-(5-(and-6)-carboxy-X-rhodaminecarbonyl)-3-aminopropyl]-N,N-dimethyl-3-N"-{4-[(2-chloroethyl)-methylamino]-benzylamine}aminopropylammonium tri-trifluoroacetate salt FIG. 1(d) (39.5 mg, 0.0465 mmol) and 4-[(2-chloroethyl)-methylamino]-benzldehyde (18.3 mg, 0.093 mmol, kindly provided by V.V. Vlassov, Institute of Bioorganic Chemistry, Siberian Division of the Russian Academy of Sciences, Novosibirsk) were dissolved in 550 µL methanol. To the stirring solution was added sodium cyanoborohidride (2.9 mg, 0.0460 mmol, Aldrich Chemical Co.); the reaction was stirred at room temperature for 22 hr. Excess borohydride was quenched with the addition of HCl (0.057 mmol). Solvent was removed on rotary evaporator, and the residue was purified via HPLC (C-18: acetonitrile/0.1% TFA) to yield 41.8 mg (87.3%) product as a red solid. TLC :silica gel; acetonitrile/10% acetic acid; 3/1; Rf=0.13. $H^1$-NMR ($CD_3OD$) ? 8.75 (d, 1H), 8.25 (dd, 1H), 7.45 (d, 1H), 7.35 (d, 2H), 6.80 (d, 2H), 6.55 (s, 2H), 4.15 (s, 2H), 3.65 (m, 4H), 3.55 (m, 12H), 3.15 (s, 6H), 3.10 (m, 2H), 3.00 (s, 3H), 2.65 (m, 2H), 2.15 (m, 8H), 1.90 (m, 4H).

FIG. 1(*f*): Digoxin Dialdehyde

To a solution of digoxin (2.30 g, 2.95 mmol, Sigma Chemical Co., St. Louis, Mo.) in 24 mL of chloroform:methanol (1:1) was added sodium periodate (0.699 g, 3.27 mmol, Aldrich Chemical Co.) and 1.0 mL water. The solution was stirred at room temperature for 18 hr. The sodium iodate precipitate was removed via filtration. Following solvent removal on rotary evaporator the residue was dissolved in 50 mL chloroform, washed 1×8 mL water, and dried over magnesium sulfate. The solvent was removed on a rotary evaporator and the residue was recrystalized from chloroform/hexane resulting in the formation of an oil. Crystal formation was initiated by the addition of a small amount of diethyl ether yielding 2.22 g (96.6%) amorphous, white solid. TLC: silica gel; acetonitrile/water; 1/1; Rf=0.88 after development with 2,4-dinitrophenyl hydrazine (Aldrich Chemical Co.).

FIG. 1(*g*): Digoxin Labeling Reagent

To a solution of FIG. 1(*f*) (300 mg, 0.385 mmol) and sodium cyanoborohydride (24.3 mg, 0.385 mmol, Aldrich Chemical Co.) in 35 mL methanol in a 100 mL roundbottom flask equipped with an addition funnel was added 4-[(2-chloroethyl)-methylamino]-benzylamine (27.0 mg, 0.099 mmol, kindly provided by V.V. Vlassov, Institute of Bioorganic Chemistry, Siberian Division of the Russian Academy of Sciences, Novosibirsk) in 15 mL methanol at a rate of 10 drop/minute. The reaction was stirred at room temperature for 18 hours. The reaction mixture was concentrated, dissolved in acetonitrile, and filtered to remove boron salts. The residue was purified on a 20 g silica gel column. Excess FIG. 1(*f*) was eluted in 100 mL acetonitrile and 100 mL 2% water in acetonitrile. Product was eluted in 200 mL 5% water in acetonitrile. Solvent removal on a rotary evaporator yielded 35.7 mg (38.1%). TLC: silica gel; acetonitrile water; 9/1; $R_f$=0.27, 0.35 corresponding to the protonated and free forms of the aromatic nitrogen. $H^1$-NMR ($CDCl_3$) 7.35 (d, 2H), 6.65 (d, 2H), 5.95 (s, 1H), 4.90 (m, 5H), 4.25 (m, 2H), 4.05 (m, 2H), 3.80 (m, 2H), 3.70 (m, 2H), 3.35 (m, 2H), 3.20 (m, 2H), 3.00 (s, 3H), 2.50-1.10 (m, 40 H), 0.95 (s, 3H), 0.80 (s, 3H).

FIG. 1(*h*): N-[N'-{4-[(2-chloroethyl)-methylamino]-benzylamine}-3-aminopropyl]-N,N-dimethyl-3-aminopropylammonium tetra-trifluoroacetate salt FIG. 1(*c*) (123 mg, 0.382 mmol) and 4-[(2-chloroethyl)-methylamino]-benzaldehyde (75.5 mg, 0.382 mmol, kindly provided by V.V. Vlassov, Institute of Bioorganic Chemistry, Siberian Division of the Russian Academy of Sciences, Novosibirsk) were dissolved in 9 mL methanol. Sodium cyanoborohydride (24.0 mg, 0.381 mmol, Aldrich Chemical Co.) was added. The reaction was stirred at room temperature for 18 hours. Solvent was removed from the reaction mixture, the residue was dissolved in TFA, and incubated for 20 minutes at room temperature to remove the BOC protecting group. The TFA was evaporated under a stream of nitrogen, and the residue was purified via HPLC (C-18: acetonitrile/ 0.1% TFA) to yield 85.0 (27.9%) as a yellow oil. TLC: silica gel; dimethylfonnamide/acetic acid/water; 1/2/2; Rf=0.31.

FIG. 1(*i*): N-[N'-(5-(and-6)-carboxyfluoresceincarbonyl)-3-aminopropyl]-N,N-dimethyl-3-N"-{4-[(2-chloroethyl)-methylamino]-benzylamine}aminopropylammonium tri-trifluoroacetate salt FIG. 1(*h*) (117 mg, 0.147 mmol) and 5-(and-6)-carboxyfluorescein succinimidyl ester (69.8 mg, 0.147 mmol, Molecular Probes, Eugene, Oreg.) were dissolved in 2.0 mL DMF. Sodium carbonate (31.0 mg, 0.292 mmol) was added, and the reaction was stirred at room temperature for 48 hours. The product was isolated by precipitation with diethylether. Product was purified by recrystalization from 10% methylsulfoxide in DMF and diethyl ether. TLC: silica gel; acetonitrile: 10% acetic acid; 3/1; Rf=0.43.

FIG. 1(*j*): N-[N'-(biotincarbonyl)-3-aminopropyl]-N,N-dimethyl-3-N"-{4-[(2-chloroethyl)-methylamino]-benzylamine}aminopropylammonium tri-trifluoroacetate salt FIG. 1(*h*) (10 µg, 12.5) and NHS-biotin (4 µg, 12.5 mol, Pierce Chemical Co., Rockford, Ill.) were dissolved in mL DMF. Diisopropyl ethyl amine (2 µL, Aldrich Chemical Co.) was added and the reaction was stirred at room temperature overnight. The product was isolated by precipitation with diethyl ether, and purified via HPLC (C18: 0.1% TFA:acetonitrile). TLC silica gel: 3/1, acetonitrile/50 mmol ammonium acetate pH4) Rf=0.135.

FIG. 1(*k*): carboxy-X-rhodaminecarbonyl/CPI2 labeling reagent

FIG. 1(*d*) (66.5 µg, 0.078 µmol) in 50 µL dimethylformamide was combined with CPI2 (50.0 µg, 0.078 mol, Epic Pharmaceuticals, Seattle, Wash.) and 1 µL of diisopropylethylamine (2% solution in DMF, Aldrich Chemical Co.). The reaction was complete after 2 hours at room temperature, as determined by TLC: silica gel; acetontrile/50 mM ammonium acetate pH 4.0; 3/1; Rf product=0.12, Rf FIG. 1(*d*)=0.0.

EXAMPLE 1

Labeling Reagents can be Covalently Attached to Double Stranded DNA (dsDNA)

By means of the procedure set forth below covalent attachment of the labeling reagents to double stranded plasmid DNA (pDNA) is demonstrated. Detectable non-radioactive labels (fluorescein, rhodamine, and digoxin) coupled to nitrogen mustards (see synthesis section) were covalently attached to polynucleic acids. Unincorporated labeling reagent is removed from labeled DNA by ethanol precipitation in 0.5 M NaCl.

Figure 1I:
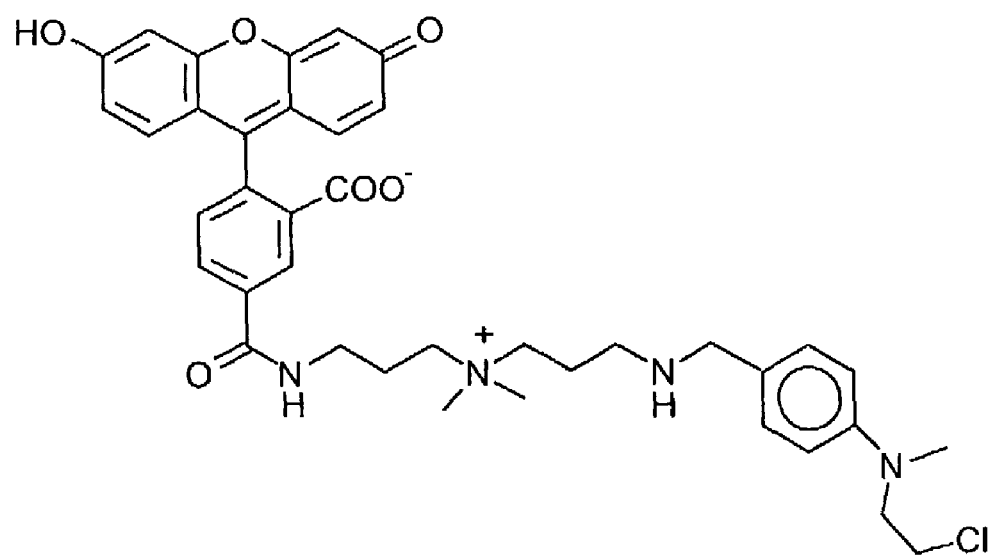
FIG. 1(i) is an illustration of the chemical structure for N-[N'-(5-(and-6)-carboxyfluoresceincarbonyl)-3-aminopropyl]-N,N-dimethyl-3-N'''-{4-[(2-chloroethyl)-methylamino]-benzylamine}aminopropylammonium salt.
Figure 1J:
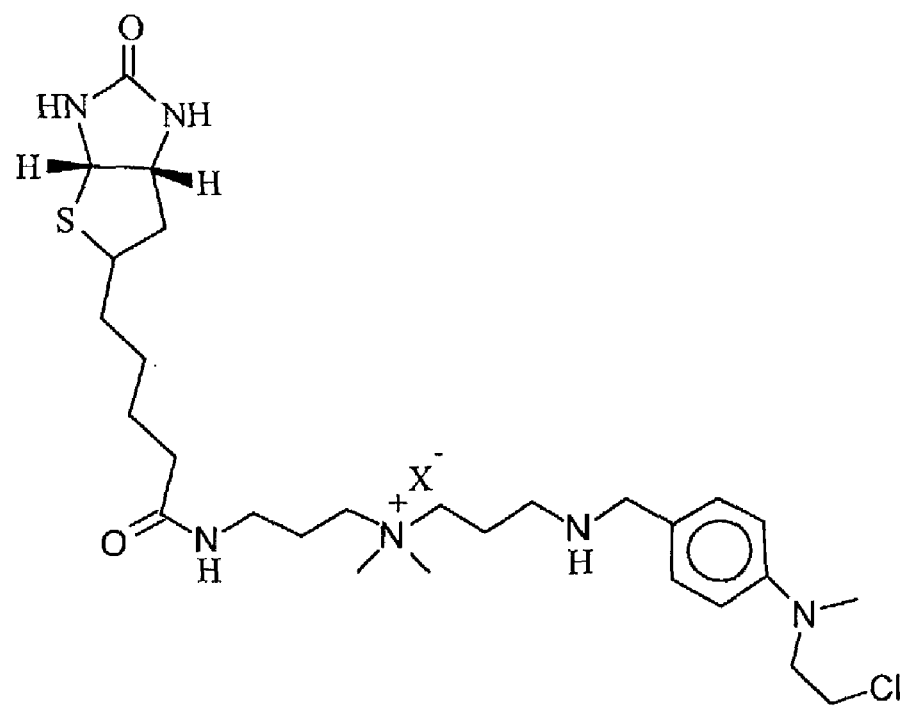
FIG. 1(j) is an illustration of the chemical structure for: N-[N'-(biotincarbonyl)-3-aminopropyl]-N,N-dimethyl-3-N'''-{4-[(2-chloroethyl)-methylamino]-benzylamine} aminopropylammonium salt.
Figure 1K:
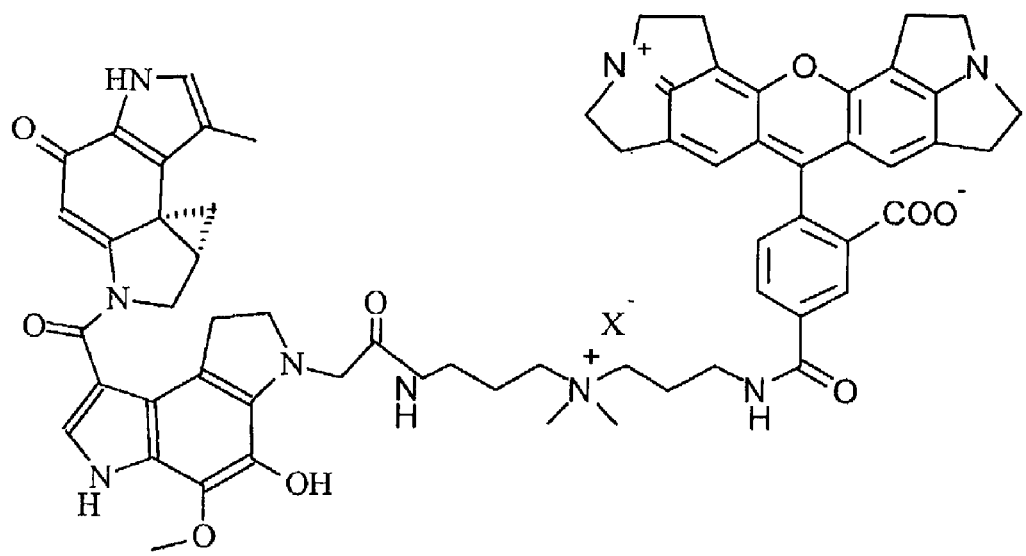
FIG. 1(k) is an illustration of the chemical structure for carboxy-X-rhodaminecarbonyl/CPI2 labeling reagent.
Figure 1L:
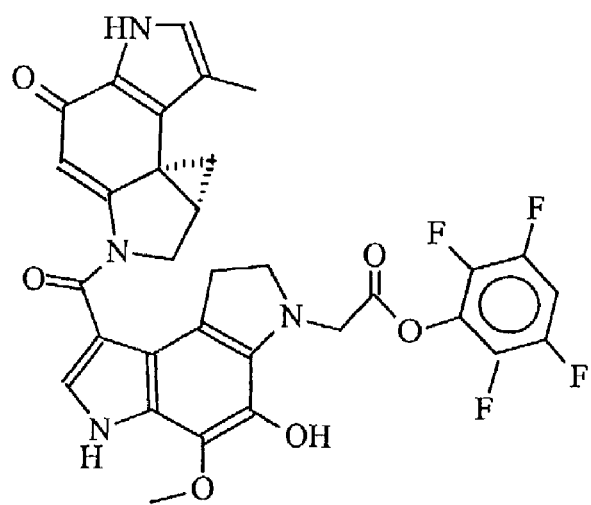
FIG. 1(l) is an illustration of the chemical structure for CPI2 moeity.

(1) Materials
 1. pDNA (3.3 µg/µL pCIluc; prepared according to Danko, I., Williams, P., Herweijer, H. et al. Hum. Mol. Genetics (1997) in press.)
 2. FIG. 1(e)
 3. FIG. 1(i)
 4. Hepes buffer (100 mM, pH 7.5)
 5. NaCl (5M aqueous solution)
 6. Ethanol (100%, Pharmco, Brookfield, Conn.)
 7. 70% Ethanol
 8. Photo-documentation camera equipped with a photo-documentation hood (FB-PDC-34 and FB-PDH-1314, FisherBiotech, Pittsburgh, Pa.)
 9. Ethidium bromide (Acros Organics, Pittsburgh, Pa.)
(2) Reaction Protocol
 0. For negative control purposes 5.0 µg portions each of FIG. 1(e) and FIG. 1(i) were incubated in 200 µL Hepes buffer for 48 hours to hydrolyze the nitrogen mustard. These samples are used as negative controls; they no longer contain an alkylating group.
 1. FIG. 1(e) (1.0 µg), FIG. 1(i) (5 µg), hydrolyzed FIG. 1(e) (1.0 µg), and hydrolyzed FIG. 1(i) (5.0 µg) were combined with plasmid DNA (5 µg) in 150 µL Hepes buffer. The reactions were vortexed to mix.
 2. The reactions were incubated at 37° C. for 1 hour.
 3. 15 µL 5M NaCl was added to each tube, the solutions was vortexed to mix, and 2 volumes ethanol was added.
 4. The reactions were incubated at −10° C. for 10 minutes, and centrifuged at 1200 rpm for 5 minutes. The supernatant was decanted, and the pellets were washed with 70% ethanol.
 5. The pellets were dissolved in 100 µL Hepes buffer. 0.4 µg labeled DNA from each reaction was run on a 1% agarose gel.
 6. A photograph was taken On a UV lightbox prior to ethidium bromide staining (3 second exposure), and after ethidium staining (1 second exposure).
(3) Results
 The covalent attachment of the labeling reagents is demonstrated by visualization of DNA bands without ethidium bromide staining. The labeled DNA in lanes 3 and 5 is visible due to the fluorescence of the covalently attached rhodamine, and fluorescein respectively. The unlabeled control plasmid in lane 2 is not visible, nor is the plasmid DNA incubated with hydrolyzed FIGS. 1(e) and (i) (lanes 4 and 6 respectively). Thus when the mustard moiety on the labeling reagents is hydrolyzed no labeling of DNA is observed.
 Now the ladder marker in lane 1 and the unlabeled plasmid in lane 2 are visible; as well as the DNA incubated with hydrolyzed labeling reagents. The integrity of the labeled plasmids is demonstrated by comparing the ratio of supercoiled to relaxed circular plasmid DNA in the unlabeled controls with that of the labeled plasmids. Any nicking will result in an increase in relaxed circular plasmid DNA. Analysis of the photograph reveals nicking levels to be low.

EXAMPLE 2

Labeling reagents can be covalently attached to single stranded DNA (ssDNA)
(1) Materials
 1. M13 bateriophage M13mp18 ssDNA (Panvera Corporation, Madison, Wis.)
(2) Procedure and Results
 The ssDNA was labeled using FIG. 1(e) according to example 1 using a 30 minute incubation period at 37° C., and a labeling reagent: DNA ratio of 0.2:1. The labeled ssDNA was analyzed by agarose gel electrophoresis, 1.0 µg of DNA per lane.

(3) Results
 Lane 3a contains labeled ssDNA, and lane 7a contains unlabeled ssDNA before ethidium bromide staining. Lane 3b contains labeled ssDNA, and Lane 7b contains unlabeled ssDNA after ethidium bromide staining. Incorporation of the labeling compounds is demonstrated by the observed fluorescence of labeled ssDNA, and the absence of unlabeled ssDNA prior to ethidium staining. The integrity of the labeled DNA is demonstrated by comparing the ethidium stained unlabeled control ssDNA with the ethidium stained labeled ssDNA.

EXAMPLE 3

Labeling Reagents can be covalently attached to RNA
(1) Materials
 1. calf liver tRNA (Boehringer Mannheim Corporation, Indianapolis, Ind.)
 2. 900b in vitro transcribed RNA (0.3 µg/mL)
 3. FIG. 1(e)
(2) Procedure
 The RNAs were labeled using FIG. 1(e) according to example 1 using a 30 minute incubation period at 37° C., and a labeling reagent: RNA ratio of 0.2:1. The labeled RNAs were analyzed by agarose gel electrophoresis, 1.0 µg of RNA per lane.
(3) Results
 Lane 1a contains labeled tRNA, lane 2a contains labeled in vitro transcribed RNA, lane 5a contains unlabeled tRNA, and lane 6a contains unlabeled in vitro transcribed RNA prior to ethidium bromide staining. Lane 1b contains labeled tRNA, lane 2b contains labeled in vitro transcribed RNA, lane 5b contains unlabeled tRNA, and lane 6b contains unlabeled after ethidium bromide staining. Covalent attachment of the labeling reagent to the RNAs is evident because RNA incubated with reagent shows visible fluorescence without ethidium bromide staining. The labeled RNA bands and the unlabeled RNA bands both migrate to an equal extent in the agarose gel, thereby demonstrating that the covalent attachment of the labeling reagent does not harm the RNA.

EXAMPLE 4

Labeling reagents can be covalently attached to linear double stranded DNA
(1) Materials
 1. λ DNA/hind III fragments (Life Technologies Inc., Gaithersburg, Md.)
(2) Procedure
 The linearized λ DNA was labeled using FIG. 1(e) according to example 1 using a 30 minute incubation period at 37° C., and a labeling reagent: DNA ratio of 0.2:1. The labeled linearized dsDNA was analyzed by agarose gel electrophoresis, 1.0 µg of DNA per lane.
(3) Results
 Lane 4a contains labeled linearized dsDNA, lane 8a contains unlabeled linearized dsDNA prior to ethidium bromide staining. Lane 4b contains labeled linearized dsDNA, and lane 8b contains unlabeled linearized dsDNA after ethidium bromide staining. Covalent attachment of the labeling reagent to the linearized dsDNAs is evident because linearized dsDNA incubated with reagent shows visible fluorescence prior to ethidium bromide staining. The labeled linearized dsDNA bands and the unlabeled linearized dsDNA bands both migrate to an equal extent in the agarose gel, thereby demonstrating that the covalent attachment of the labeling reagent does not harm the linearized ds DNA.

EXAMPLE 5

CPI2 based labeling reagents can be covalently attached to DNA (1) Materials
1. FIG. 1($k$)
2. pDNA (pCIluc; prepared according to Danko, I., Williams, P., Herweijer, H. et al. Hum. Mol. Genetics (1997) in press.)

(2) Procedure and Results pDNA was labeled using FIG. 1($k$) with a labeling reagent to DNA ratio of 1:1. The procedure for DNA labeling given in example 1 was followed, however the incubation period was increased to 12 hours. The covalent attachment of the CPI2-based reagent (FIG. 1($k$)) was demonstrated by agarose gel electrophoresis. The DNA band was visible prior to ethidium bromide staining.

EXAMPLE 6

Incorporation of labeling reagents onto the polynucleotide is proportional to the amount of labeling reagent used The extent of labeling reagent incorporation into the polynucleotide can be controlled by regulating the ratio of labeling reagent to polynucleotide.

(1) Experimental Protocol pDNAs (pCIluc) were labeled according to the procedure in example 1 using FIG. 1($e$) as the labeling reagent. DNA was labeled at the following weight to weight ratios (labeling reagent: DNA): (0.01:1), (0.02:1), (0.05:1), (0.10:1), (O.20:1), (O.50:1), and (1:1). 0.2 µg DNA sample were analyzed on an agarose gel. The remaining portion of labeled DNA was analyzed on a Beckman DU6 UV/visible spectrophotometer (Beckman Instruments, Inc. Arlington Heights, Ill.).

(2) Results

Extent of incorporation was observed by visualization of an agarose gel prior to ethidium staining. Fluorescence was visible for all labeling ratios. An increase in the intensity of the fluorescence from the lowest to highest labeling reagent to DNA ratios was also observed. The absolute extent of label incorporation was determined by measuring the absorbency of the purified samples at 576 nm ($\lambda_{max}$ for 5-(and-6)-car-boxy-X-rhodamine, Molecular Probes Inc.). The absorption intensity at 576 nm was divided by the absorption intensity at 260 nm to correct for slight variations in the absolute amount of DNA present. Incorporation of labeling reagent is dependent on the amount of labeling reagent used, and is nearly linear before falling off at the higher ratios.

EXAMPLE 7

The labeling method is highly sensitive, 0.1 pg of DNA can be detected (1) Materials
1. FIG. 1($g$)
2. pDNA (3.3 µg/µL pCIluc; prepared according to Danko, I., Williams, P., Herweijer, H. et al. Hum. Mol. Genetics (1997) in press.)
3. Calf Thymus DNA (Sigma Chemical Co.)
4. Anti-Digoxigenin-AP Fab fragments (Boebringer Mannheim Corporation)
5. CSPD chemiluminescence substrate (Boehringer Mannheim Corporation)
6. nylon filter (Micron Separations Inc, Westborough, Mass.)

(2) Procedure pCIluc pDNA was labeled using FIG. 1($g$) according to the procedure given in example 1 using a 60 minute incubation period at 37° C., and a labeling reagent to DNA ratio of 5:1. The labeled DNA was applied to a nylon filter using a slot blot apparatus. Samples were applied to the nylon filter using 500 µL aliquots containing from 0.10 pg to 50.0 pg labeled DNA. A 50 pg unlabeled control DNA (pCIluc and calf thymus) samples were also applied to the nylon filter. FIG. 1($g$) (50 pg) was treated according to example 1 in a tube without DNA, and applied to the nylon filter as a purification control. The filter was baked at 70° C. for 1 hour and processed using anti-digoxigenin Fab fragments and the CSPD chemiluminescence substrate following procedures described in Boehringer Mannheim's "The DIG System User's Guide for Filter Hybridization," chapter 9, pages 58-60. The filter was visualized by exposing to X-ray film for 10 minutes.

(3) Results

The labeling method is highly sensitive, labeled DNA was visible and above background from 0.1 pg to 50 pg.

EXAMPLE 8

Labeled DNA can hybridize to complementary DNA

DNA modified using FIG. 1($g$) (the digoxin containing labeling reagent) was used to demonstrate hybridization of probe DNA to complimentary DNA immobilized on a nylon filter.

(1) Materials
1. pDNA (3.3 µg/µL pCIluc; prepared according to Danko, I., Williams, P., Herweijer, H. et al. Hum. Mol. Genetics (1997) in press.)
2. Calf Thymus DNA (Sigma Chemical Co.)
3. FIG. 1($g$)
4. Anti-Digoxigenin-AP Fab fragments (Boebringer Mannheim Corporation)
5. CSPD chemiluminescence substrate (Boehringer Mannheim Corporation)
6. nylon filter (Micron Separations Inc.)

(2) Procedure pDNA (pCIluc) was labeled using FIG. 1($g$) according to the procedure given in example 1 using a labeling reagent to DNA ratio of 1:1. The labeled DNA was alkali denatured and used to probe unlabeled pDNA (pCIluc) and calf thymus control DNA. The unlabeled DNAs were denatured and fixed onto a nylon membrane at concentrations from 10 pg to 20 ng using a slot-blot apparatus. After blotting, the membrane was baked at 70° C. for 2 hr, the membrane was prehybridized and hybridized according to the procedure given in Boehringer Mannheim's "The DIG System User's Guide for Filter Hybridization," chapter 8, pages 45-48. The denatured, labeled probe DNA was diluted to a final concentration of 20 ng/mL in the hybridization solution. The membranes were incubated in the hybridization solution at 42° C. overnight. The membranes were then processed following the procedure given in example 7.

(3) Results

The pDNA probed with complimentary labeled DNA was detectable at 10 pg, the lowest level tested. No hybridization of the probe DNA to the negative control (calf thymus DNA) was observed.

EXAMPLE 9

Labeled DNA can be used as probe DNA for southern hybridization (1) Materials
1. Mouse genomic DNA (generously provided by Hans Herweijer, University of Wisconsin-Madison)
2. Human genomic DNA (Panvera Inc., Madison, Wis.)
3. Calf Thymus DNA (Sigma Chemical Co.)
4. Rat Beta Actin DNA (Panvera Inc.)
5. Restriction enzyme Eco R1 (Promega Inc., Madison, Wis.)
6. nylon filter (Micron Separations Inc.)

(2) Procedure

Hybridization of the labeled probe to target DNA was performed using standard southern blot procedures as described in Maniatis' "Molecular Cloning," chapter 9, pages 9.31 to 9.58. Briefly, probe DNA was labeled with FIG. 1(g) in a 1:1 ratio according to example 1. Genomic DNAs were digested with Eco R1, run on an agarose gel, and transferred to a nylon filter. The nylon filter was hybridized with the labeled probe DNA at 42° C. overnight. The nylon membrane was then developed according to example 7.

(3) Results

The developed film showed one hybridization band between mouse genomic DNA and the labeled rat beta actin probe. A weaker band was also observed in the lane containing calf thymus genomic DNA indicating some cross reactivity between the labeled rat beta actin probe and calf thymus genomic DNA.

EXAMPLE 10

Labeled DNA is stable to long term storage conditions (1) Materials
1. pDNA (pCIluc) labeled with reagent 5 at a labeling reagent to DNA ratio of 0.2:1 and 0.04:1.

(2) Procedure and Results

Portions of labeled pDNA were stored in 100 mM HEPES buffer pH 7.5 at −20° C., and at 4° C. Aliquots (0.4 μg) were analyzed by agarose gel electrophoresis at the time of preparation, after 24 hours, after 1 week, and after 1 month at the stated storage conditions. Gels were photographed before and after ethidium bromide staining at the stated time periods. The amount of fluorescence, and the ratio of the supercoiled to relaxed plasmid bands were examined. No degradation was observed for the labeled DNA stored at −20° C. at either labeling level. The labeled DNA stored at 4° C. was stable for 1 week at the 0.2:1 ratio, and for at least 1 month at the 0.04:1 ratio.

EXAMPLE 11

Labeling reagents can be covalently attached to DNA for use in DNA localization following cellular delivery (1) Materials
1. pDNA (pCIluc) labeled with reagent 5 at two concentrations
2. TransIT LT-1 transfection reagent (Mirus Corporation, Madison, Wis.)
3. Cells (NIH 3T3 immortalized mouse fibroblast, ATTC, Rockville, Md.)
4. fluorescence microscope (Leitz Orthoplan, Leitz Corporation, Germany)

(2) Procedure

Transfections were performed according to manufacturers recommendations. 2 μg DNA were transfected per 35 mm well. Cells were fixed, and analyzed by fluorescence microscopy after 1 hour incubation.

(3) Results

Labeled DNA was observed in a punctate, perinuclear pattern. Strong fluorescent signal with low background was observed at both concentrations. No fluorescence was observed in cells transfected with unlabeled DNA.

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A labeling molecule, for alkylating a chemical in a single-step reaction thereby providing the chemical with a detectable reporter molecule, comprising: 1) a spacer with a net positive charge and with affinity for nucleic acids selected from the group consisting of DNA minor groove binder and DNA major groove binder; 2) a reporter molecule selected from the group consisting of fluoresceins, rhodamines, lucifer yellow, 4,4-difluoro-4-bora-3a,4a-diaza-s-indacene derivatives, malachite green, coumarins, dansyl derivatives, mansyl derivatives, dabsyl drivatives, NBD flouride, stillbenes, anthrocenes, rosamines, TNS chloride, eosins, ethidium bromide derivatives, thiazole orange derivatives, ethenoadenosines, cyanine derivatives, aconitine, Oregon Green, Cascade Blue, radioactive molecules, immunogenic molecules, haptens, biotin, oligosaccharides, and proteins; and, 3) an aromatic mustard reactive group.

2. A kit comprising:
a) a receptacle containing the labeling molecule of claim 1; and, b) instructions for use.

3. A compound having the structure comprising:

D-B-A wherein,
D is a label detectable in an aqueous biological sample selected from the group consisting of fluoresceins, rhodamines, lucifer yellow, 4,4-difluoro-4-bora-3a,4a-diaza-s-indacene derivatives, malachite green, coumarins, dansyl derivatives, mansyl derivatives, dabsyl drivatives, NBD flouride, stillbenes, anthrocenes, rosamines, TNS chloride, eosins, ethidium bromide derivatives, thiazole orange derivatives, ethenoadenosines, cyanine derivatives, aconitine, Oregon Green, Cascade Blue, biotin, oligosaccharides, radioactive compounds, haptens, immunogenic molecules, and proteins;
B is a linker containing a net charge greater than zero and with affinity for nucleic acids selected from the group consisting of DNA minor groove binder and DNA major groove binder; and,
A is an aromatic nitrogen mustard alkylating group.

* * * * *